(12) United States Patent  
Aferzon et al.

(10) Patent No.: US 9,039,770 B2  
(45) Date of Patent: *May 26, 2015

(54) APPARATUS FOR ANTERIOR INTERVERTEBRAL SPINAL FIXATION AND FUSION

(75) Inventors: Joseph Aferzon, Avon, CT (US); Joshua Aferzon, Avon, CT (US)

(73) Assignee: ALPHATEC SPINE, INC., Carlspad, CA (US)

( * ) Notice: Subject to any disclaimer, the term of this patent is extended or adjusted under 35 U.S.C. 154(b) by 408 days.

This patent is subject to a terminal disclaimer.

(21) Appl. No.: 13/335,382

(22) Filed: Dec. 5, 2011

(65) Prior Publication Data

US 2013/0006360 A1 Jan. 3, 2013

Related U.S. Application Data

(60) Continuation of application No. 12/567,691, filed on Sep. 25, 2009, now Pat. No. 8,070,819, which is a division of application No. 11/321,936, filed on Dec. 29, 2005, now Pat. No. 7,594,932.

(51) Int. Cl.
  *A61F 2/44* (2006.01)
  *A61F 2/46* (2006.01)
  *A61F 2/30* (2006.01)

(52) U.S. Cl.
  CPC ................. *A61F 2/447* (2013.01); *A61F 2/446* (2013.01); *A61F 2/4611* (2013.01); *A61F 2002/30365* (2013.01); *A61F 2002/30579* (2013.01); *A61F 2002/30841* (2013.01); *A61F 2002/30845* (2013.01); *A61F 2002/4475* (2013.01); *A61F 2002/4627* (2013.01); *A61F 2220/0033* (2013.01)

(58) Field of Classification Search
  CPC ........... A61F 2/447; A61F 2002/30841; A61F 2002/30845
  USPC ....................................................... 623/17.16
  See application file for complete search history.

(56) References Cited

U.S. PATENT DOCUMENTS

| | | | | |
|---|---|---|---|---|
| 6,770,096 B2 * | 8/2004 | Bolger et al. | ............... | 623/17.16 |
| 7,594,932 B2 * | 9/2009 | Aferzon et al. | ............ | 623/17.16 |
| 8,070,819 B2 * | 12/2011 | Aferzon et al. | ............ | 623/17.16 |

* cited by examiner

*Primary Examiner* — Ellen C Hammond
(74) *Attorney, Agent, or Firm* — Michael J. Loi

(57) ABSTRACT

A spinal fixation device includes a housing and a plurality of blades. Each blade includes a body having a central opening configured to rotate on a shaft within the housing. Control openings on opposing sides of the central opening are sized to engage prongs of a rotating tool. At least one cutting extension with a sharp leading edge extends from the body in an orientation about an axis of the shaft. Upon rotation of the blade by the rotating tool about the shaft in a direction in which the at least one cutting extension is oriented, the at least one cutting extension will break an endplate of a vertebra and hook into the vertebra.

16 Claims, 18 Drawing Sheets

APPARATUS FOR ANTERIOR INTERVERTEBRAL SPINAL FIXATION AND FUSION

CROSS-REFERENCES TO RELATED APPLICATIONS

The present application is a continuation of U.S. patent application Ser. No. 12/567,691 to Aferzon et al., filed Sep. 25, 2009, which is a divisional of U.S. patent application Ser. No. 11/321,936 to Aferzon et al., filed Dec. 29, 2005, both entitled "APPARATUS AND METHOD FOR ANTERIOR INTERVERTEBRAL SPINAL FIXATION AND FUSION", the contents of which are incorporated herein by reference in its entirety.

FIELD OF INVENTION

This invention relates to a spinal fusion device. More specifically, the present invention relates to an implant and fixation device used to reconstruct spinal disk space and facilitate fusion across the spinal disk space.

BACKGROUND OF THE INVENTION

Articulations between bony vertebras of a human spine frequently deteriorate with age or trauma and become a source of pain. A spinal disk is one of these articulations and with the aging process it loses its normal consistency and volume and collapses allowing for abnormally painful motion within the anterior spinal column. The spinal disk is a complex cylindrical weight-bearing fibrous structure with a non-compressible viscous center. The spinal disk articulates with bony vertebra above and below through a large surface area circular interface known as an endplate. The endplate is a thin (1-3 mm) approximately round 2-4 cm in diameter plate of dense bone and cartilage accounting for a majority of the vertebral weight-bearing capacity.

Surgical treatment of disk disorders frequently requires elimination of movement across an abnormal spinal disk. This is accomplished by allowing bone to grow between adjacent vertebra and through a disk space of the abnormal spinal disk. It is desirable to reconstruct the disk space to its prior normal height by opening the space previously occupied by the removed spinal disk while retaining normal curvature of the spine determined by the differential height between the front and the back of the spinal disk (FIG. 3). This is commonly achieved by using inserts or implants which open the disk space and which allows for growth of the bridging bone. The ultimate effectiveness of an implant is based on the following factors: (i) ability to reconstruct and maintain a normal configuration of a vertebral column; (ii) ease of insertion; (iii) facilitation of bony fusion and; (iv) restriction of movement across the disk space.

Implants utilized in fusion of a human spine and delivered in a straight trajectory through the front of the spine and into the disk space are well known to those skilled in the art. They vary in shape but possess similar characteristics with upper and lower surfaces conforming to a shape of vertebral endplates and a vertical design aiming to open or reconstruct the collapsed disk space. These implants are sufficiently porous or hollow to allow bone to grow through the implants and bridge two vertebras referred to as bone fusion. These implants perform well with vertical loading of the spine or in flexion. However, these implants are not able to restrict the movement between two vertebras when vertebras are pulled apart or are in extension and lateral bending. Further, these implants provide negligible restriction during sliding motion (translation) and rotation.

Devices that cut into or have protrusions directed into or through the endplate, are also known in the related art. These protrusions penetrate the endplate and potentially create channels for a bone growth, yet the protrusions do not alter structural properties of the endplate. The protrusions also reduce the risk of extrusion of the implant out of the disk space. These protrusions negligibly restrict translation or sliding motion but they do not restrict extension and lateral bending. This necessitates additional fixation (immobilization) usually consisting of posterior pedicle screws.

There would be a substantial benefit in an anterior fixation device which would on its own rigidly fixate the spine in all direction of motion.

SUMMARY OF THE INVENTION

A device for reconstruction, fixation and bone fusion through anterior approach to the human spine. This device enables rigid fixation in all planes of motion including extension of the spine, it possesses structural characteristics necessary to reconstruct and maintain disk height, it provides space for bone grafting material and produces a plurality of perforations through endplates above and below to enhance bony fusion.

In a first aspect, embodiments of the present invention provide a plurality of blades for use in a fixation device, each blade includes a body having a central opening configured to rotate on a shaft within a housing of the fixation device, control openings on opposing sides of the central opening sized to engage prongs of a rotating tool, and at least one cutting extension with a sharp leading edge extending from the body in an orientation about an axis of the shaft, wherein upon rotation of the blades by the rotating tool about the shaft in a direction in which the at least one cutting extension is oriented, the at least one cutting extension will break an endplate of a vertebra and hook into the vertebra.

In many embodiments, the at least one cutting extension includes two opposing cutting extensions with sharp leading edges which hook into adjacent vertebrae.

In many embodiments, the orientation of the at least one cutting extension may be either in a first orientation for clockwise rotation about the shaft or a second orientation for counterclockwise rotation about the shaft In many embodiments, the plurality of blades includes at least one first blade having the at least one cutting extension in the first orientation and at least one second blade having at the at least one cutting extension in the second orientation.

In many embodiments, the at least one first blade and the at least one second blade alternate between the first orientation and the second orientation when preloaded onto the shaft.

In many embodiments, the at least one first blade and the at least one second blade are rotated sequentially with the prongs of the rotating tool via the control openings.

In many embodiments, the body includes a shape configured to expand a disk space as the blade is rotated.

In many embodiments, the blade includes means for locking the blade.

In another aspect, embodiments of the present invention provide a method of using a plurality of blades within a fixation device to attach to a vertebra, the method includes providing a plurality of blades, each blade includes a body having a central opening configured to rotate on a shaft within a housing of the fixation device, control openings on opposing sides of the central opening sized to engage prongs of a rotating tool, and at least one cutting extension with a sharp leading edge extending from the body in an orientation about an axis of the shaft, inserting the blades between the adjacent vertebrae with the fixation device, rotating the blades using the rotating tool via the control openings about the shaft in a direction in which the at least one cutting extension is oriented, and breaking an endplate of vertebra with the at least one cutting extension of the blades, hooking into the vertebra and rigidly securing the vertebra to the fixation device.

In many embodiments, the body of the blade includes a shape configured to expand a disk space as the blade is rotated, and the step of rotating the blade includes expanding the disk space.

In many embodiments, the plurality of blades includes at least one first blade having the at least one cutting extension in a first orientation for clockwise rotation and at least one second blade having at the at least one cutting extension in a second orientation for counterclockwise rotation, the step of inserting the blade between adjacent vertebrae includes inserting the at least first and second blades between adjacent vertebrae, and the step of rotating the blade includes clockwise or counterclockwise rotation of the at least one first blade and the at least one second blade in a direction in which the at least one cutting extensions of each blade are oriented.

In many embodiments, the at least one first blade and the at least one second blade alternate between the first orientation and the second orientation when preloaded onto the shaft.

In many embodiments, the at least one first blade and the at least one second blade are rotated sequentially with the prongs of the rotating tool via the control openings.

In another aspect, embodiments of the present invention provide a fixation device, the device includes a housing with a leading deep surface, a trailing outer surface, weight bearing sides, and top and bottom surfaces, first and second shafts running from the leading deep surface to the trailing outer surface of the housing, at least one first blade having at least one cutting extension with a sharp leading edge preloaded on the first shaft in a first orientation about an axis of the first shaft and at least one second blade having at least one cutting extension with a sharp leading edge preloaded on the second shaft in a second orientation about an axis of the second shaft that is opposite to the first orientation, wherein upon clockwise or counterclockwise rotation of the at least one first blade and the at least second blade about the axis of the first and second shafts in a direction in which the at least one cutting extension of each blade is oriented, the at least one cutting extension of each blade will break an endplate of a vertebra, hook into the vertebra and rigidly secure the vertebra to the device to prevent separation of the vertebra from the device during spinal motion.

In many embodiments, the at least one first blade and the at least second blade includes two opposing cutting extensions with sharp leading edges which hook into adjacent vertebrae to rigidly secure the adjacent vertebrae in relation to each other and to the device to prevent separation of the vertebrae from the device during spinal motion.

In many embodiments, the at least one first blade and the at least second blade are imbricated between each other In many embodiments, the at least one first blade and the at least second blade alternate between the first orientation and the second orientation.

In many embodiments, the device further includes means for rotating the at least one first blade and the at least second blade from a horizontal into a vertical orientation.

In many embodiments, the at least one first blade and the at least second blade are rotated individually or as a group.

In many embodiments, the device further includes means for locking the at least one first blade and the at least second blade in a final engaged position preventing dislodging from the vertebra In many embodiments, the at least one first blade and the at least second blade includes a body having a shape configured to provide weight bearing support to the secured vertebra.

In many embodiments, the shape of the body is configured to expand the disk space as the blade is rotated.

In many embodiments, the housing is expandable at least in part in vertical and horizontal directions.

In many embodiments, the first and second shafts separate from each other upon expansion of the housing.

In many embodiments, the first and second shafts run perpendicular to the leading deep surface of the housing.

In many embodiments, the housing is configured in a shape of a box, a cylinder or other geometric shape including configurations with a height of the leading deep surface smaller than a height of the trailing outer surface, the shape conforming to a shape of a spinal disk space.

In many embodiments, the blades vary in size to accommodate the configuration of the housing.

In many embodiments, the shape of the body is an oval so that the disk space is expanded as the blade is rotated.

In many embodiments, the leading deep surface conforms to a posterior aspect of an intervertebral disk and the trailing outer surface conforms to an anterior surface of the intervertebral disk.

In many embodiments, the housing includes a plurality of openings enabling ingrowths of bone.

In another aspect, embodiments of the present invention provide a method of using a fixation device between two adjacent vertebrae, the method including providing a fixation device, the fixation device having a housing with a leading deep surface conforming to a posterior aspect of an intervertebral disk and trailing outer surface conforming to an anterior surface of the intervertebral disk, first and second shafts running from the leading deep surface to the trailing outer surface of the housing, and at least one first blade having at least one cutting extension with a sharp leading edge preloaded on the first shaft in a first orientation about an axis of the first shaft and at least one second blade having at least one cutting extension with a sharp leading edge preloaded on the second shaft in a second orientation about an axis of the second shaft that is opposite to the first orientation. The method further including inserting the fixation device between the adjacent vertebrae, rotating each blade of the at least one first blade and the at least second blade in a clockwise or counterclockwise rotation about the axis of the first and second shafts, and breaking an endplate of each vertebra with the extension of each blade, hooking into the vertebra and rigidly securing the vertebra to the device to prevent separation of the vertebra from the device during spinal motion.

In many embodiments, the at least one first blade and the at least second blade includes two opposing cutting extensions with sharp leading edges which hook into adjacent vertebrae.

DETAILED DESCRIPTION

An implant device for reconstruction, fixation and bone fusion of bone vertebras through an anterior approach to the human spine. This implant device enables rigid fixation in all planes of motion including extension of the spine, it possesses structural characteristics necessary to reconstruct and maintain disk height, it provides space for bone grafting material and produces a plurality of perforations through endplates above and below to enhance bony fusion.

The implant device consists of the outer structure or shell which is designed to conform to the disk space, provide openings for bony ingrowths and maintain the disk height by providing adequate structural strength and sufficient weight bearing surface. The shell or housing contains a shaft (10) which runs through its central axis from the back (9) to the front (8) and is fixed to the shell (FIG. 7).

Figure 12:
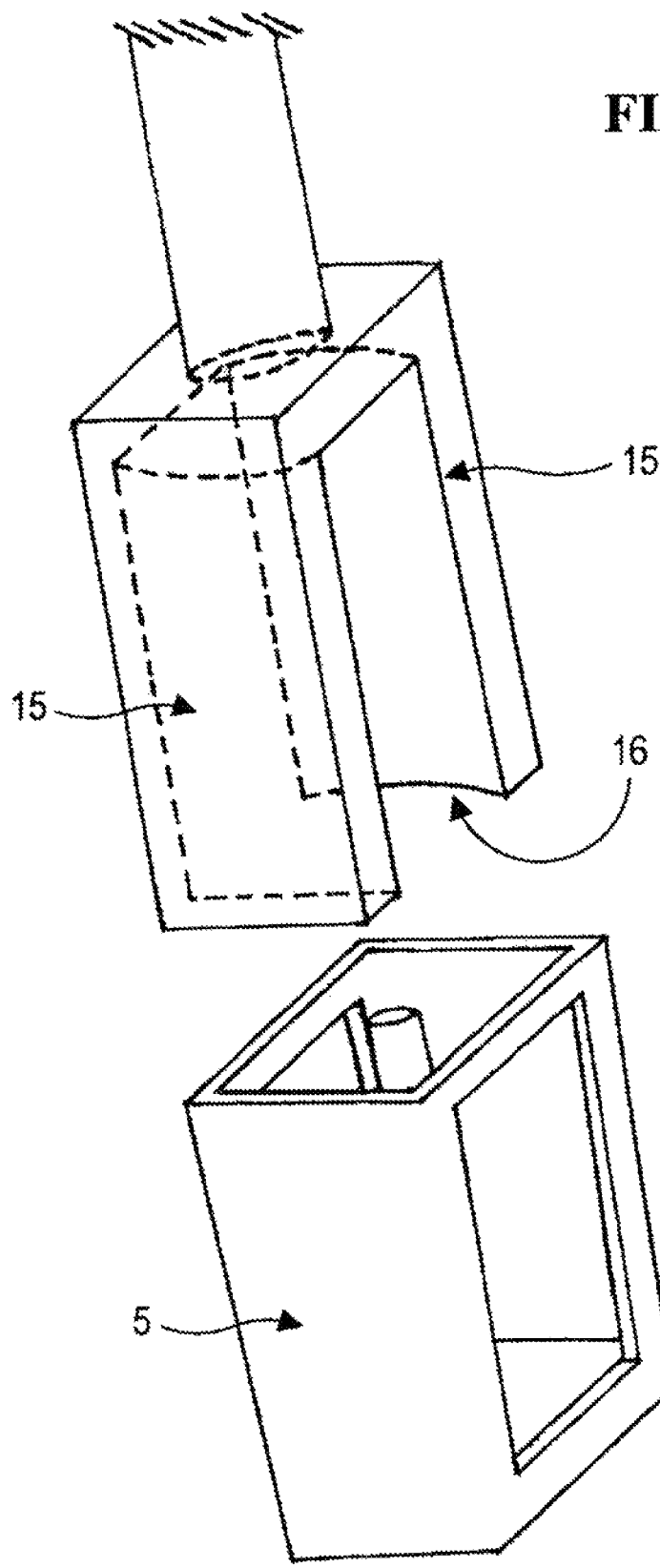
FIG. 12 illustrates a preferred embodiment of an insertion instrument for the housing. Prongs (15) fit inside the lateral walls (5) of the housing but clear the central opening (16) occupied by the blades.
Figure 13:
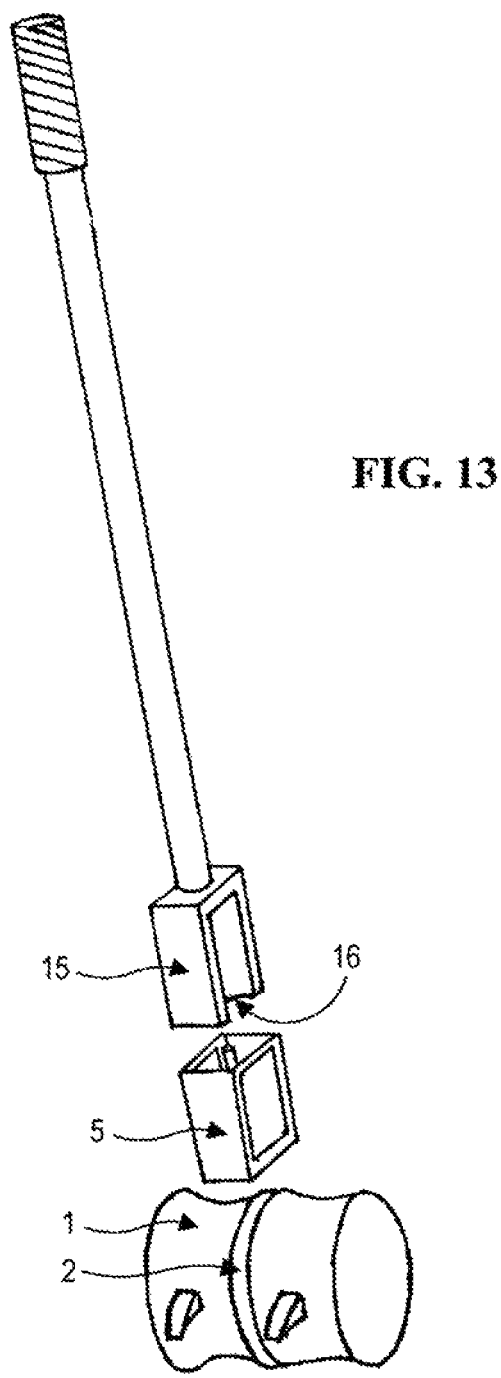
FIG. 13 illustrates a preferred method of placing the housing into a collapsed disk space (2) between vertebras (1).
Figure 14:
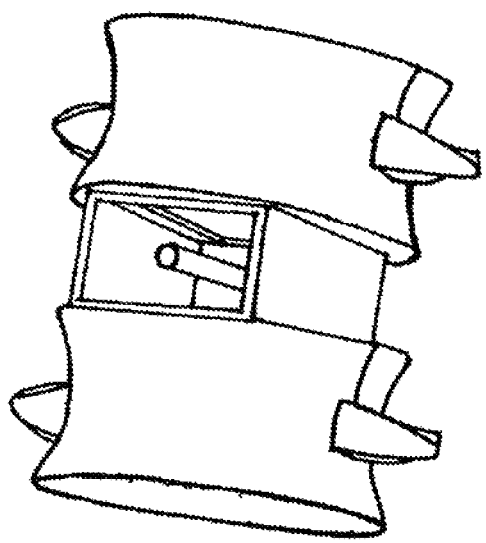
FIG. 14 illustrates a housing inside expanded disk space.

In the preferred embodiment the shell is impacted into the disk space (FIG. 14) using the shell introducer (FIG. 13). The shell introducer includes prongs (15) that fit inside the sides (5) of the shell but is open (16) in the center to allow for blades (FIG. 12).

Figure 11:
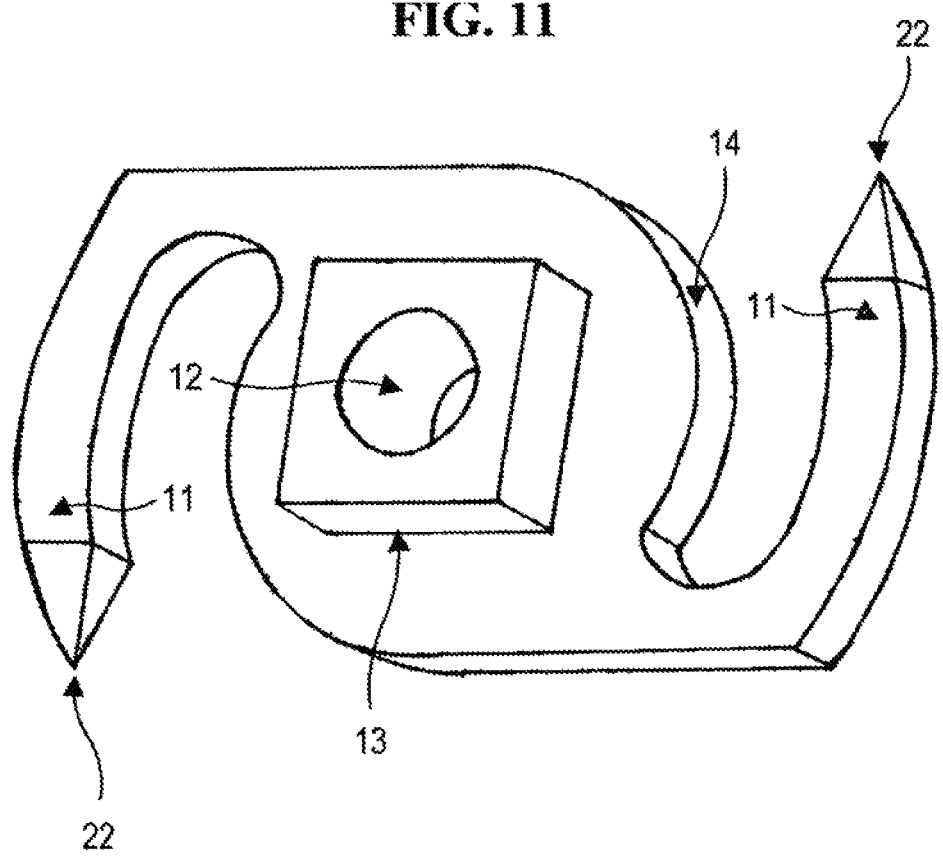
FIG. 11 illustrates a perspective view of the counterclockwise blade.
Figure 15:
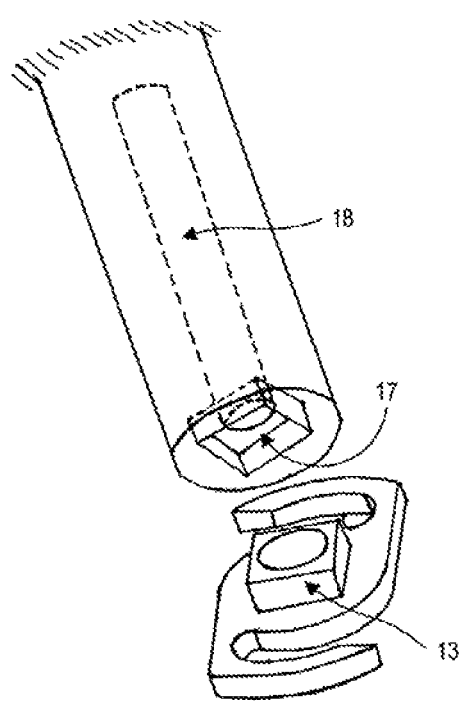
FIG. 15 illustrates a preferred embodiment of a blade introducer having a receptacle (17) for the control nut (13) and central opening (18) for the shaft (10).
Figure 16:
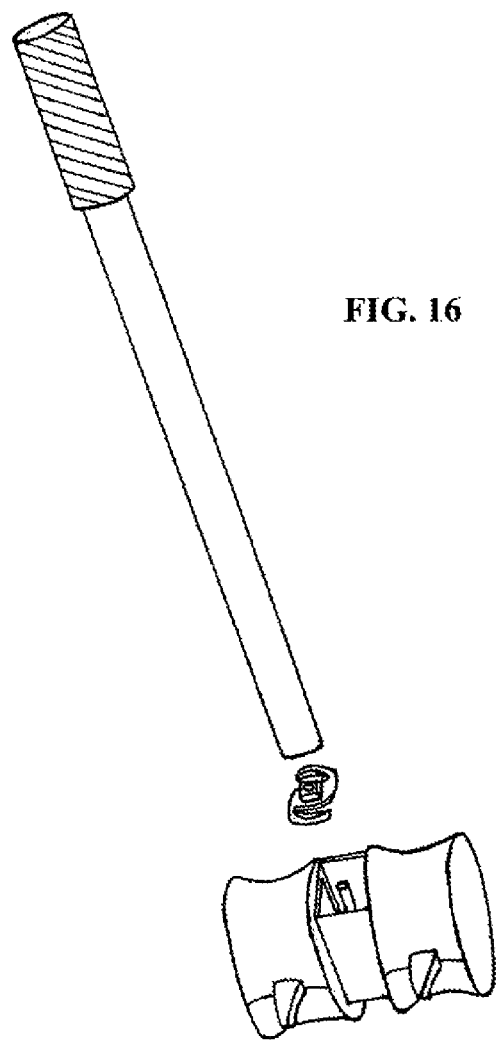
FIG. 16 illustrates a blade of FIG. 8 introduced horizontally into the housing of FIG. 7 using the blade introducer of FIG. 15.
Figure 17:
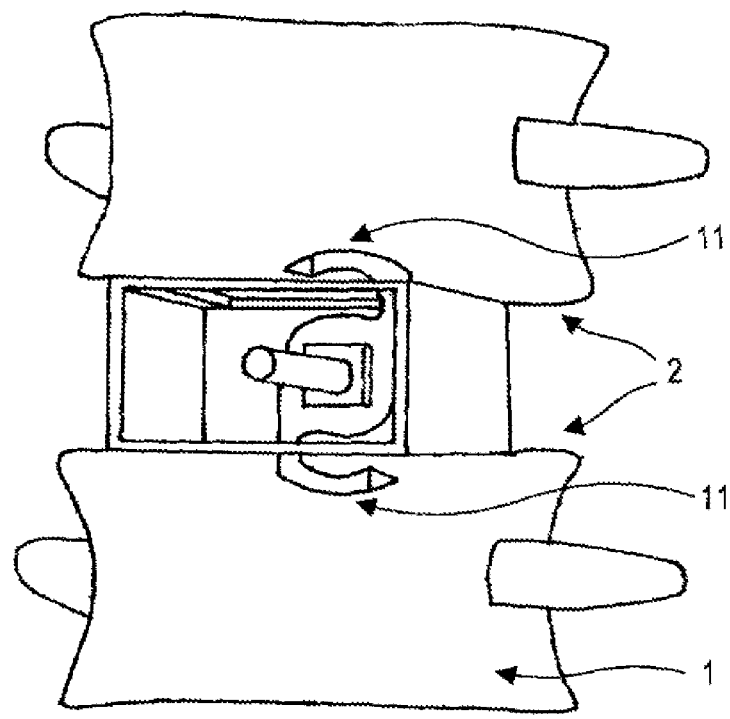
FIG. 17 illustrates a blade rotated vertically with cutting extensions (11) piercing vertebral endplates and hooking into vertebras (1).

Once the shell is placed in a correct position between vertebras (1), individual blades (FIG. 11) are selected, mounted onto the introducer (FIG. 15) and threaded onto the shaft (10) in horizontal orientation (FIG. 16). The blade is placed as deep as it can go and then rotated into vertical orientation breaking the endplate and hooking into the vertebra (1) (FIG. 17). Blades alternate between clockwise and counterclockwise orientation. Variable size blades can be selected to better approximate configuration of the disk space.

Figure 1:
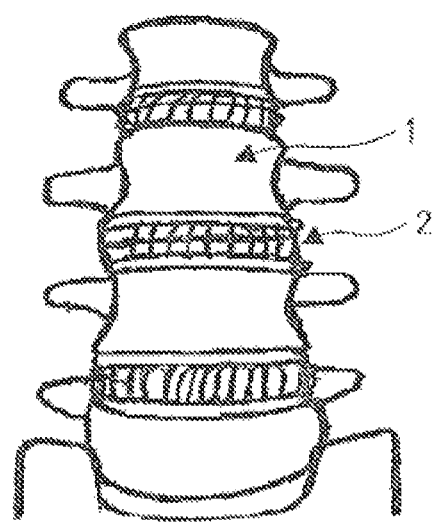
FIG. 1 illustrates an anterior view of the lumbar spine demonstrating vertebra (1) alternating with disk (2).
Figure 2:
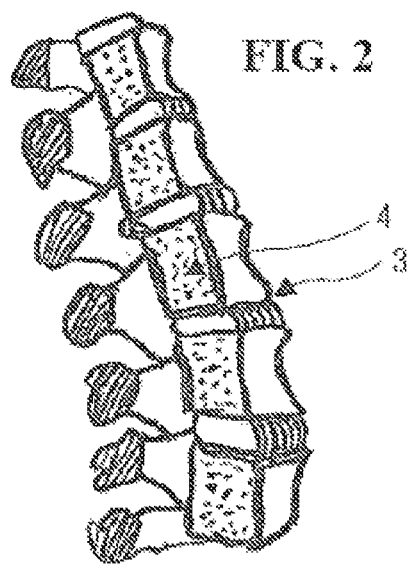
FIG. 2 illustrates an anterior view of the vertically sliced lumbar spine demonstrating internal composition of the vertebra with dense endplate (3) and softer inner part (4).
Figure 3:
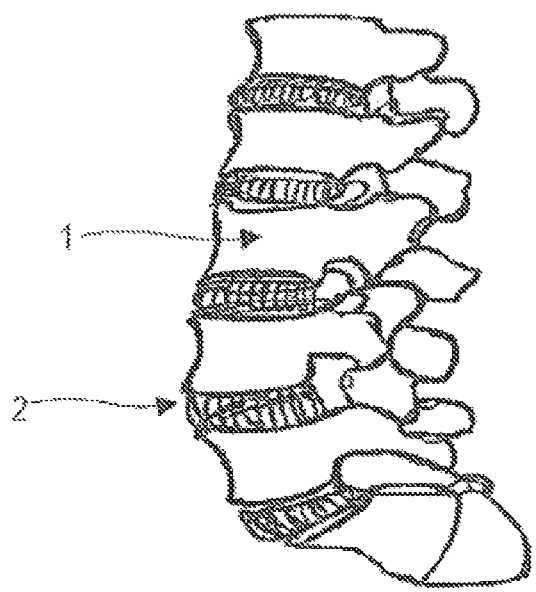
FIG. 3 illustrates a lateral (side) view of the vertebral column demonstrating normal curvature (lordosis) of the lumbar spine.
Figure 4:
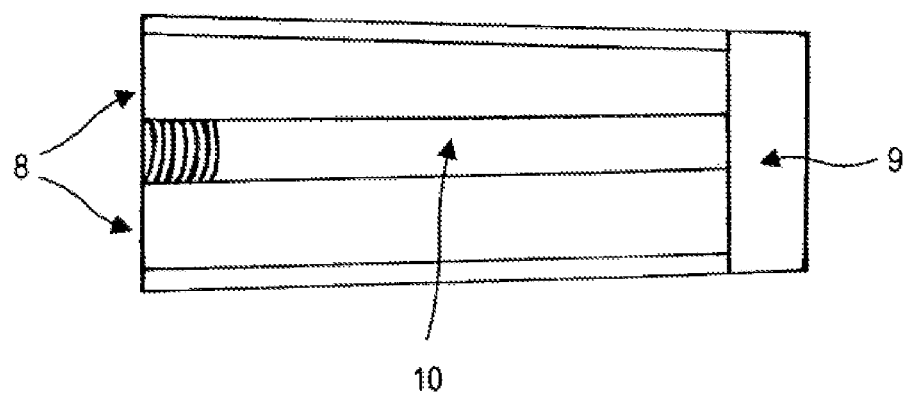
FIG. 4 illustrates a lateral (side) view of the preferred embodiment of a housing with front opening (8), back wall (9), and central shaft (10) fixed to the back wall (9).
Figure 5:
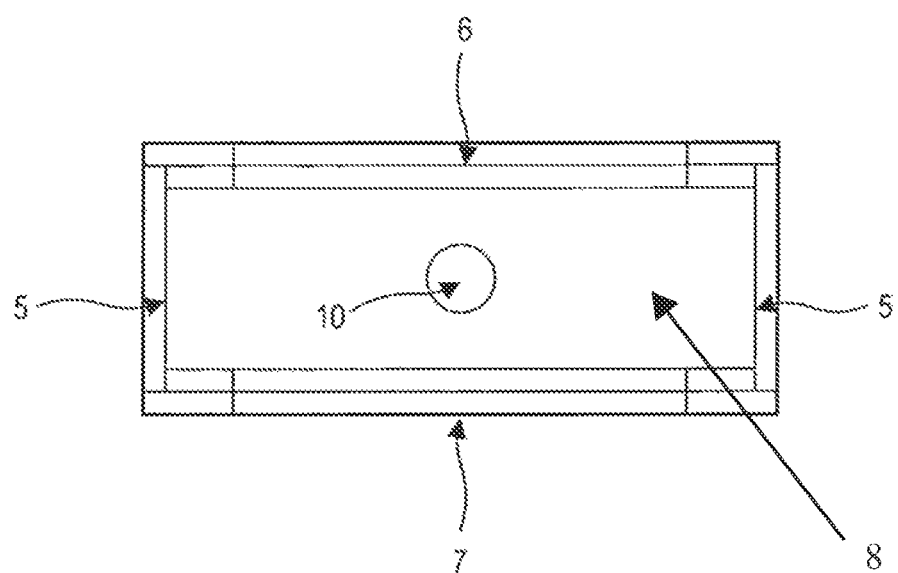
FIG. 5 illustrates an anterior (front) view through the front opening (8) of the housing with lateral weight bearing walls (5), top (6) and bottom (7) openings, and central shaft (10).
Figure 6:
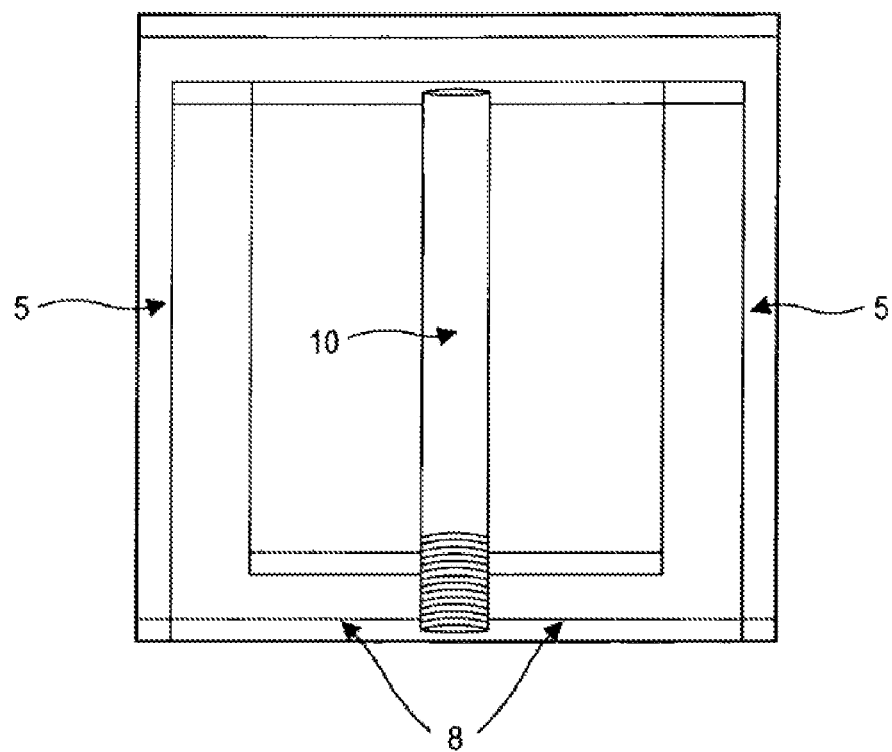
FIG. 6 illustrates a superior (top) view through the top opening (6) of the housing showing the central shaft (10).
Figure 7:
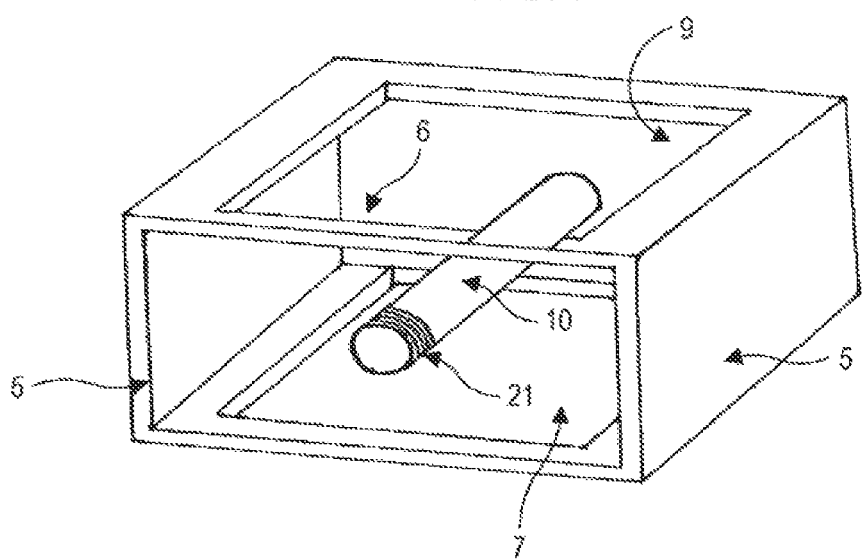
FIG. 7 illustrates a perspective view of the housing with lateral weight bearing walls (5), top (6) and bottom (7) openings, back wall (9), and a central shaft (10) including threaded end (21).
Figure 8:
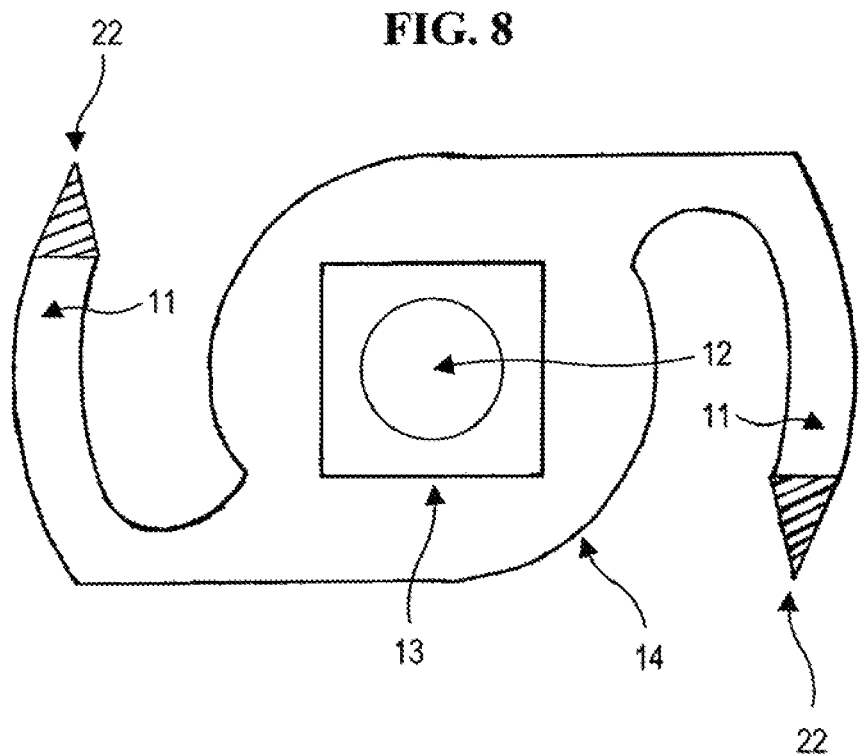
FIG. 8 illustrates a front view of the preferred embodiment of a clockwise blade with cutting extensions (11) having sharp ends (22) that cut through the endplate 3 and into the cancellous bone (4) of vertebra (1). A central opening (12) fits over the shaft 10 of the housing. A control nut (13) is used to handle the blade and to thread onto the shaft (10). A body of the blade (14) provides additional central weight bearing support against vertebral endplates.
Figure 9:
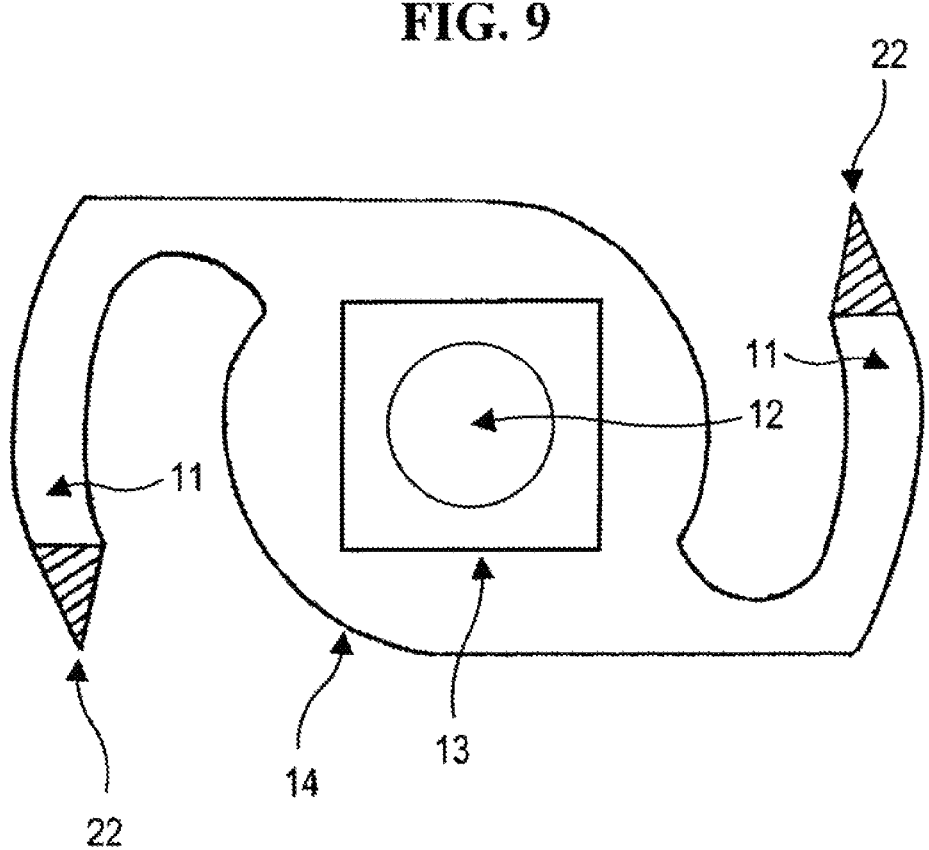
FIG. 9 illustrates a front view of the preferred embodiment of a counterclockwise clockwise blade.
Figure 10:
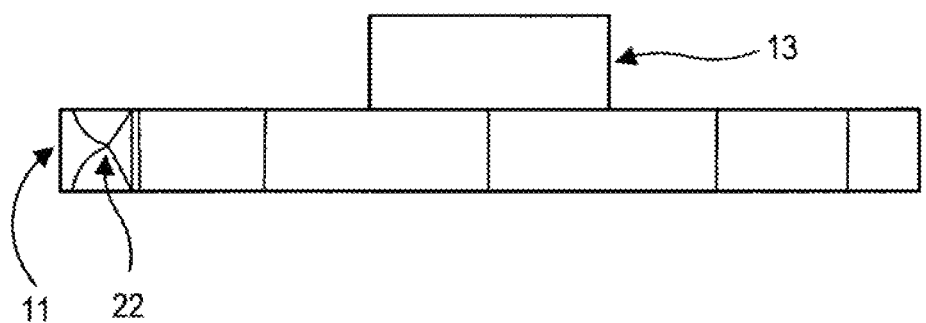
FIG. 10 illustrates a top view of the counterclockwise blade showing cutting extension (11) having sharp end (22) and control nut 13.

Once all the blades are engaged, a tightening nut is threaded onto the end (21) of the shaft (10) of FIG. 7.

Figure 18:
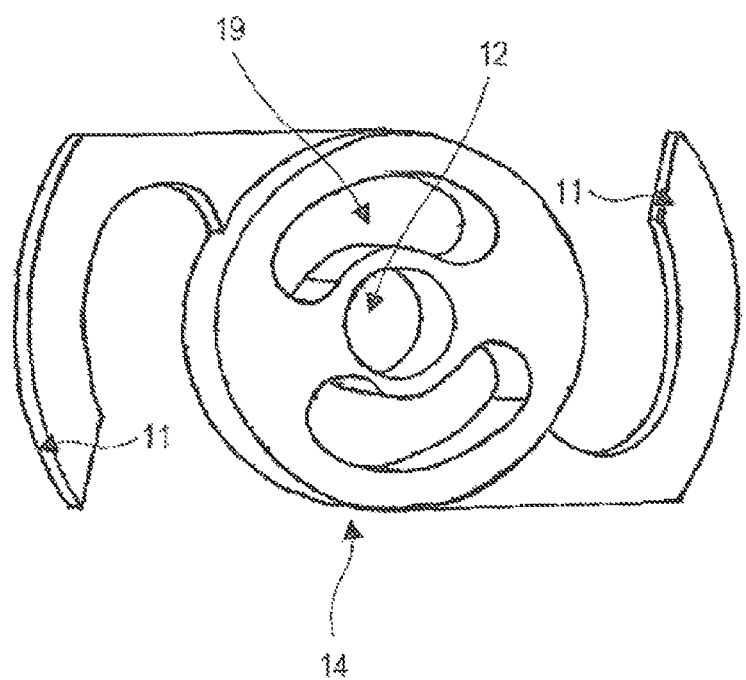
FIG. 18 illustrates an alternative embodiment of a blade having central opening (12) and control openings (19) on opposing sides of the central opening (12) to rotate the blade about the shaft (10). These blades are preloaded into the housing prior to placement of the housing into the disk space.
Figure 19:
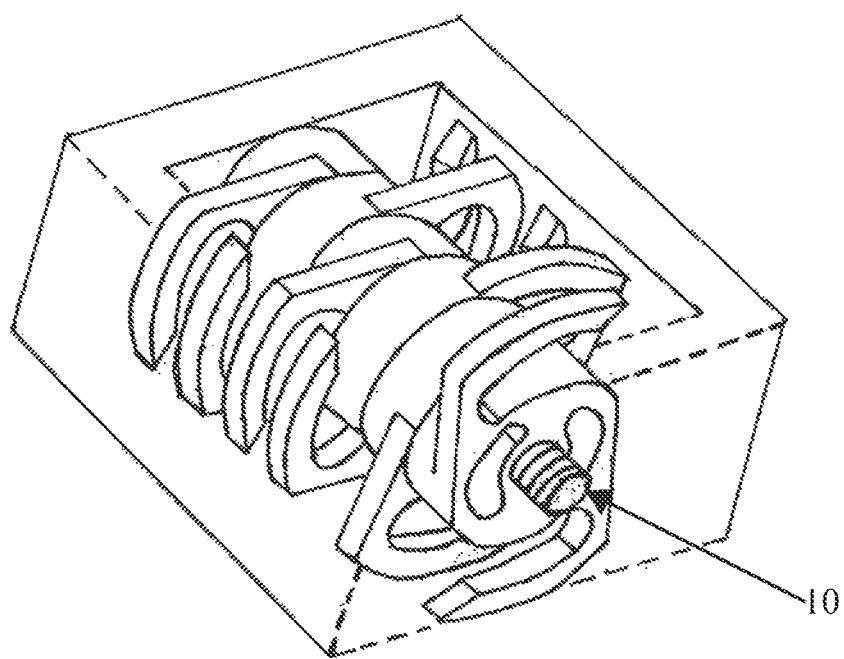
FIG. 19 illustrates a transparent housing and central shaft (10) with pre-loaded blades showing front two blades rotated into final vertical position.
Figure 20:
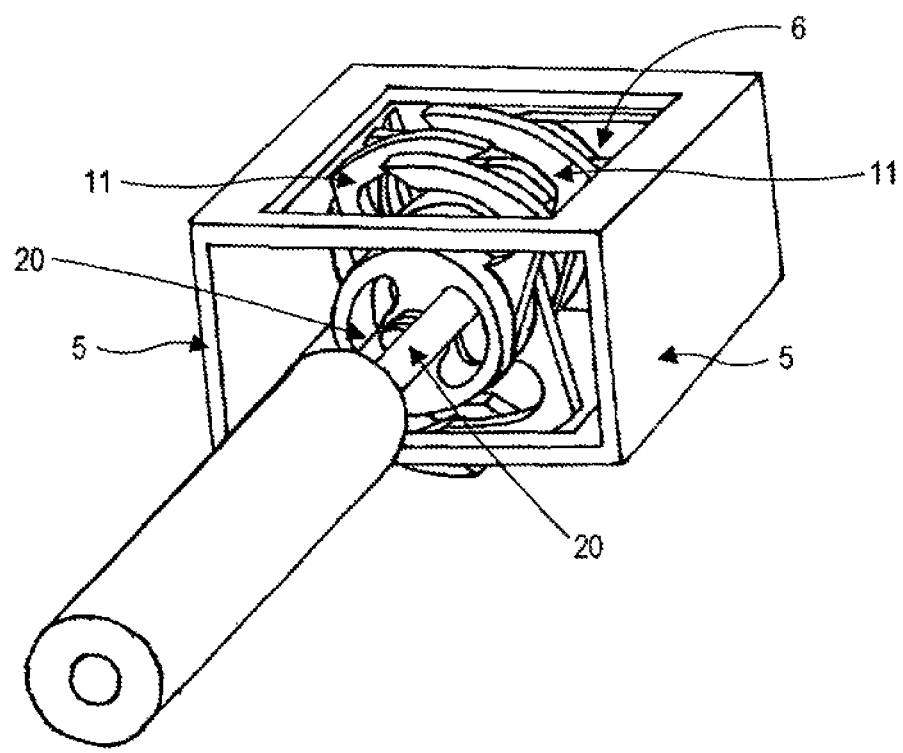
FIG. 20 illustrates a blade rotating tool fits into control openings (19) of clockwise and counterclockwise blades with prongs (20) of the rotating tool engaging and rotating the first three blades via the control openings (19).

In an alternative embodiment, alternating clockwise and counterclockwise blades (FIG. 18) are pre-loaded onto the shaft (10) and inside the housing (FIG. 19). The blades include a central opening (12) and control openings (19) on opposing sides of the central opening (12) to rotate the blade about the shaft (10). With the help of a blade rotating tool with prongs (20) engaging the control openings (19) (FIG. 20), the blades are rotated sequentially going from superficial to deep.

In another embodiment the housing expands horizontally and contains two shafts, which separate from each other upon expansion of the housing. In the initial collapsed configuration, preloaded clockwise and counterclockwise blades threaded on different shafts imbricate between each other. After the cage is expanded, blades are pulled apart.

In another embodiment, a body (14) of a blade is configured as an oval so that the disk space is expanded as a blade is rotated.

The invention claimed is:

1. A fixation device comprising:
    a housing configured to house a plurality of blades;
    each of the plurality of blades including:
        a body having a central opening configured to rotate on a shaft within the housing;
        control openings on opposing sides of the central opening sized to engage prongs of a rotating tool; and
        at least one cutting extension with a sharp leading edge extending from the body in an orientation about an axis of the shaft;
        wherein upon rotation of a blade by the rotating tool about the shaft in a direction in which the at least one cutting extension is oriented, the at least one cutting extension will break an endplate of a vertebra and hook into the vertebra.

2. The device of claim 1, wherein the at least one cutting extension includes two opposing cutting extensions with sharp leading edges which hook into adjacent vertebrae.

3. The device of claim 1, wherein the orientation of the at least one cutting extension is in a first orientation for clockwise rotation about the shaft or a second orientation for counterclockwise rotation about the shaft.

4. The device of claim 3, wherein the plurality of blades includes at least one first blade having the at least one cutting extension in the first orientation and at least one second blade having at the at least one cutting extension in the second orientation.

5. The device of claim 4, wherein the at least one first blade and the at least one second blade alternate between the first orientation and the second orientation when preloaded onto the shaft.

6. The device of claim 4, wherein the control openings are configured to permit advancement of the prongs through the body such that the at least one first blade and the at least one second blade are rotated sequentially on the shaft with the prongs of the rotating tool via the control openings.

7. The device of claim 1, wherein the body includes a shape configured to expand a disk space as the blade is rotated.

8. The device of claim 1, further comprising means for locking the blades.

9. The fixation device of claim 1, wherein the control openings are configured to engage the prongs of the rotating tool by advancement of the prongs through the control openings and along a path parallel to the shaft.

10. The fixation device of claim 1, wherein the control openings are configured to permit sequential rotation by the prongs from superficial to deep within the housing.

11. The fixation device of claim 1, wherein the control openings and the central opening extend through the body in a direction along a path parallel to the shaft.

12. A fixation device comprising:
 a housing with a leading deep surface and a trailing outer surface, weight bearing sides, and top and bottom surfaces;
 a shaft running from the leading deep surface to the trailing outer surface of the housing;
 a plurality of blades, each of the blades comprising:
  a body having a central opening configured to rotate on the shaft within the housing of the fixation device;
  control openings on opposing sides of the central opening sized to engage prongs of a rotating tool; and
  at least one cutting extension with a sharp leading edge extending from the body in an orientation about an axis of the shaft;
  wherein upon rotation of a blade by the rotating tool about the shaft in a direction in which the at least one cutting extension is oriented, the at least one cutting extension will break an endplate of a vertebra and hook into the vertebra.

13. The device of claim 12, wherein at least one first blade and at least one second blade of the plurality of blades includes two opposing cutting extensions with sharp leading edges which hook into adjacent vertebrae to rigidly secure the adjacent vertebrae in relation to each other and to the device to prevent separation of the vertebrae from the device during spinal motion.

14. The device of claim 13, wherein the at least one first blade and the at least second blade are imbricated between each other.

15. The device of claim 13, wherein the at least one first blade and the at least second blade are rotated individually or as a group.

16. The device of claim 13, wherein the body of the at least one first blade and the at least second blade has a shape configured to expand a disk space as the blade is rotated.

* * * * *